United States Patent
Ponomarenko et al.

(10) Patent No.: US 10,131,678 B2
(45) Date of Patent: Nov. 20, 2018

(54) METHOD FOR PRODUCING BRANCHED OLIGOARYLSILANES

(71) Applicant: Luminescent Innovation Technologies LLC, Moscow (RU)

(72) Inventors: Sergey Anatolyevich Ponomarenko, Moscow (RU); Oleg Valentinovich Borshchev, Moscow (RU); Nikolai Mikhailovich Surin, Troitsk (RU); Maksim Sergeevich Skorotetsky, Vyazma (RU)

(73) Assignee: Luminescent Innovation Technologies LLC, Moscow (RU)

( * ) Notice: Subject to any disclaimer, the term of this patent is extended or adjusted under 35 U.S.C. 154(b) by 0 days.

(21) Appl. No.: 15/714,079

(22) Filed: Sep. 25, 2017

(65) Prior Publication Data
US 2018/0009832 A1   Jan. 11, 2018

Related U.S. Application Data (62) Division of application No. 14/895,188, filed as application No. PCT/RU2013/000540 on Jun. 25, 2013, now Pat. No. 9,777,026.

(30) Foreign Application Priority Data

Jun. 7, 2013 (RU) ............................ 2013126222

(51) Int. Cl.
C09K 11/06 (2006.01)
C07F 7/08 (2006.01)
C08G 77/60 (2006.01)

(52) U.S. Cl.
CPC ............ *C07F 7/0814* (2013.01); *C08G 77/60* (2013.01); *C09K 11/06* (2013.01); *C09K 2211/1022* (2013.01); *C09K 2211/1092* (2013.01)

(58) Field of Classification Search
CPC ................. C07F 7/0814; C09K 11/06
See application file for complete search history.

(56) References Cited

U.S. PATENT DOCUMENTS 6,558,818 B1   5/2003   Samuel et al.
6,720,093 B2   4/2004   Samuel et al.
9,777,026 B2 * 10/2017   Ponomarenko ....... C07F 7/0814

FOREIGN PATENT DOCUMENTS

EP   1027398   6/2004
RU   2396290   8/2010

OTHER PUBLICATIONS

Borschev et al., "Bithiophenesilane Dendrimers: Synthesis and Thermal and Optical Properties", Organometallics 2007, 26, pp. 5165-5173.
Jung et al., "New hole blocking material for green-emitting phosphorescent organic electroluminescent devices", Organic Electronics 8 (2007) pp. 349-356.
S. Gronowitz, A.-B.-Hornfeldt, Thiophenes, Elsevier Academic press, 2004, p. 755.
Luponosov et al., "First Organosilicon Molecular Antennas", Chem. Mater., 2009, 21(3), pp. 447-455.
Kim et al., "High-Purity-Blue and High-Efficiency Electroluminescent Devices Based on Anthracene", Adv. Funct. Mater., 2005, 15, pp. 1799-1805.

* cited by examiner

*Primary Examiner* — Golam M Shameem
(74) *Attorney, Agent, or Firm* — Boyle Fredrickson S.C.

(57) ABSTRACT

Branched oligoarylsilanes of general formula (I)

$$X_m\text{-}(Q_k\text{-}Si\text{-}(Ar_n\text{-}R)_3)_2 \quad (I).$$

A method of preparation of branched oligoarylsilanes is that a compound of general formula (III)

$$Y\text{-}Q_k\text{-}Si\text{-}(Ar_n\text{-}R)_3 \quad (III),$$

where Y stands for a residue of boronic acid or its ester or Br or I, reacts under Suzuki conditions with a reagent of general formula (IV)

$$A\text{-}X_m\text{-}A \quad (IV),$$

where A stands for: Br or I, provided that Y stands for a residue of boronic acid or its ester; or a residue of boronic acid or its ester, provided that Y stands for Br or I. A technical result is preparation of novel compounds, featured by a high luminescence efficiency, efficient intramolecular energy transfer from some molecular fragments to others, and an increased thermal stability.

10 Claims, 2 Drawing Sheets

METHOD FOR PRODUCING BRANCHED OLIGOARYLSILANES

CROSS-REFERENCE TO RELATED APPLICATIONS

This application is a divisional of U.S. patent application Ser. No. 14/895,188, filed on Dec. 1, 2015 (U.S. Pat. No. 9,777,026, issued Oct. 3, 2017), entitled Branched Oligoarylsilanes and Method for Producing Same. The subject matter of this applications is hereby incorporated by reference in its entirety.

BACKGROUND OF THE INVENTION

Field of the Invention

The present invention relates to the field of chemical technology of organosilicon compounds and can find an industrial application for preparation of novel functional materials, which possess luminescent properties. In particular, the invention relates to novel branched oligoarylsilanes.

Description of Related Art

Figure 1:
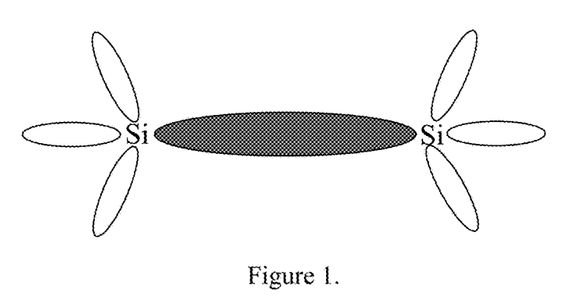
In FIG. 1 a schematic representation of the novel branched oligoarylsilanes is shown.
Figure 2:
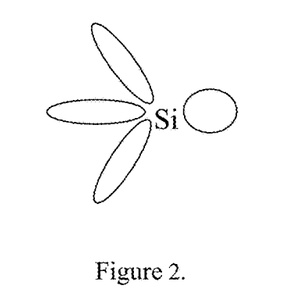
In FIG. 2 a schematic representation of the compounds of general formula (III) is shown.

As novel branched oligoarylsilanes within the current invention we mean the oligoarylsilanes, which are highly ordered spatially superbranched completely acyclic molecules in which two Si atoms are coupled to the central oligoaryl fragment, while each of the Si atoms is coupled with three other oligoaryl fragments, which possess a larger band gap (FIG. 1). As arylsilanes within the current invention we mean such compounds, which contain direct Si-aryl or Si-hetetoaryl bonds.

Either linear or branched arylsilanes are known, as well as based on them linear or branched polymers with arylsilane fragments in the main chain or as side substituents. In contrast with classic polyarylsilanes, novel branched oligoarylsilanes are individual compounds. This fact allows their isolation with a high degree of purity available for low molecular weight compounds. This is especially important for their application in organic photonics and electronics. The specific 3D architecture of such molecules provides them a number of valuable properties, such as good solubility and ability of films formation in combination with the possibility to tune their optical and electrical properties by means of molecular design.

Branched oligoarylsilanes, described within the present invention, have a molecular structure close to that of aromatic dendrimers, exhibiting luminescent properties. Organic light emitting dendrimers and devices based on them are known, for instance, from European patent EP 1027398 B1, 2004, USA patents U.S. Pat. No. 6,558,818 B1, 2003 and U.S. Pat. No. 6,720,093 B2, 2004. The dendrimers applied may contain organosilicon fragments as well as heteroaryl fragments. However, synthesis of the dendrimers is quite a time-consuming and expensive process.

Similar molecular structure to those of the branched oligoarylsilanes claimed have oligoarylsilanes A (Adv. Funct. Mater. 2005. 15. 1799-1805.) and B (Organic Electronics 8 (2007) 349-356), having the following structural formula:

which may be represented as a general formula (A-1) and (B-1):

In structures A and B two silicon atoms are linked to the central oligoaryl fragment, while each of the silicon atoms is linked to three aryl (phenyl) fragments. In contrast to oligoarylsilanes A and B, within the present invention we claim oligoarylsilanes, possessing specific optical properties due to the presence of three oligoaryl fragments attached to each silicon atom. Moreover, the claimed compounds, in contrast to the known analogues, contain terminal groups R, which improve significantly solubility of the oligoarylsilanes.

The closest structural analogue of the novel branched oligoarylsilanes claimed are branched oligoarylsilanes of the following general formula (Patent RU 2396290):

Such oligoarylsilanes apart from the central oligoaryl fragment contain two other oligoaryl fragments $Ar_n$, which are linked to each silicon atom.

SUMMARY OF THE INVENTION

In contrast with the known oligoarylsilanes, the chemical structures elaborated by us contain a central oligoaryl fragment linked to two silicon atoms, each of which is linked to three other oligoaryl fragments. An increase of the number of oligoaryl fragments linked to silicon atoms affects significantly the optical properties of such systems. In particular, it allows increasing molar extinction coefficients of the compounds and, as a consequence, improving the light absorbing ability of the functional materials based on them.

The object of the claimed invention is the synthesis of novel branched oligoarylsilanes, possessing a number of properties, due to which they can be used as luminescent materials for organic electronics and photonics.

The technical results achieved are the following: large molar extinction coefficients, high luminescence efficiency, efficient intramolecular energy transfer from one fragments of the molecule to others, and a high thermal stability.

The effects pointed above are determined by the fact that novel branched oligoarylsilanes of the general formula (I) are obtained, where R is a substituent from the row: linear or branched $C_1$-$C_{20}$ alkyl groups; linear or branched $C_1$-$C_{20}$ alkyl groups, separated one from the other at least by one oxygen atom; linear or branched $C_1$-$C_{20}$ alkyl groups, separated one from the other at least by one sulfur atom; branched $C_3$-$C_{20}$ alkyl groups, separated one from the other at least by one silicon atom; $C_2$-$C_{20}$ alkenyl groups, Ar stands for identical or different arylene or hetetoarylene radicals, selected from the row:

substituted or unsubstituted thienyl-2,5-diyl of general formula (II-a)

substituted or unsubstituted phenyl-1,4-diyl of general formula (II-b)

substituted or unsubstituted 1,3-oxazole-2,5-diyl of general formula (II-c)

substituted fluorene-4,4'-diyl of general formula (II-d)

substituted cyclopentadithiophene-2,7-diyl of general formula (II-e)

where $R_1$, $R_2$, $R_3$, $R_4$, $R_5$, independently of each other stand for H or a substituent from the pointed above row for R; $R_6$, $R_7$, $R_8$, $R_9$ stands for a substituent from the pointed above row for R, Q stands for a radical from the pointed above row for Ar,

X stands for at least one radical, selected from the pointed above row for Ar and/or radical from the row: 2,1,3-benzothiadiazole-4,7-diyl of general formula (II-f), antracene-9,10-diyl of the formula (II-g)

1,3,4-oxadiazole-2,5-diyl of general formula (II-h)

(II-h)

1-phenyl-2-pyrazoline-3,5-diyl of general formula (II-i)

(II-i)

perylene-3,10-diyl of general formula (II-j)

(II-j)

n stands for an integer from 2 to 4,
m stands for an integer from 1 to 3,
k stands for an integer from 1 to 3.

At the same time fragment $X_m(Q_k)_2$ is an internal part of the molecule and the length of this fragment is determined by numbers m and k; while the outer part of the molecule consists of six oligoaryl fragments $Ar_n$—R, linked to silicon atoms, which are the points of conjugation discontinuity between the inner and the outer parts of the molecule, as well as between the separate fragments composing the outer part of the molecule (Organometallics 2007, 26, 5165-5173). At the same time, the conjugation length of the oligoaryl fragment in the inner part of the molecule is larger than the conjugation length of any of the oligoaryl fragments in the outer part of the molecule. This provides an efficient energy transfer from the outer part of the molecule to the inner one (Chem. Mater. 2009, 21, 447-455). For realization of such an efficient energy transfer a good overlap between the absorption spectrum of oligoarylsilane fragments of the outer part of the molecules and the luminescence spectrum of the inner oligoarylsilane fragment is required.

The positions, marked with the sign * (star) in formulas (II-a)-(II-j) are the points of the molecules where the structural fragments (II-a)-(II-j) are linked to each other in the form of linear conjugated oligomeric chains $Ar_n$ (or $X_m$ or $Q_k$) or chain ends $Ar_n$ (or $Q_k$), linked to silicon atoms in the points of branching or chain ends $Ar_n$, linked to the terminal substituents R.

These and other features and advantages of the invention will become apparent to those skilled in the art from the following description and the accompanying drawing. It should be understood, however, that the detailed description and specific examples, while indicating a preferred embodiment of the present invention, are given by way of illustration and not of limitation. Many changes and modifications may be made within the scope of the present invention without departing from the spirit thereof, and the invention includes all such modifications.

DETAILED DESCRIPTION OF THE PREFERRED EMBODIMENTS

A schematic representation of the novel branched oligoarylsilanes is depicted in FIG. 1, where the tinted oval stands for the inner part of the molecule, and the non-tinted ovals—for the outer luminophores. The preferred examples for R are linear or branched $C_1$-$C_{20}$ alkyl groups, for instance, methyl, ethyl, n-propyl, iso-propyl, n-butyl, t-butyl, iso-butyl, sec-butyl, n-penthyl, 1-methylbutyl, 2-methylbutyl, 3-methylbutyl, 1-ethylpropyl, 1,1-dimethylpropyl, 2,2-dimethylpropyl, n-hexyl, n-heptyl, n-octyl, 2-ethylhexyl, n-nonyl, n-decyl, n-undecyl, n-dodecyl. The most preferred examples for R are: methyl, ethyl, n-hexyl, 2-ethylhexyl.

The preferred examples of Ar are: unsubstituted thienyl-2,5-diyl of general formula (II-a), where $R_1=R_2=H$; substituted thienyl-2,5-diyl of general formula (II-a), where $R_1=H$, in particular, 3-methylthienyl-2,5-diyl, 3-ethylthienyl-2,5-diyl, 3-propylthienyl-2,5-diyl, 3-butylthienyl-2,5-diyl, 3-penthylthienyl-2,5-diyl, 3-hexylthienyl-2,5-diyl, 3-(2-ethylhexyl)thienyl-2,5-diyl; unsubstituted phenyl-1,4-diyl of general formula (II-b), where $R_3=R_4=H$; substituted phenyl-1,4-diyl of general formula (II-b), where $R_3=H$, in particular, (2,5-dimethyl)phenyl-1,4-diyl, (2,5-diethyl)phenyl-1,4-diyl, (2,5-dipropyl)phenyl-1,4-diyl, (2,5-dibutyl)phenyl-1,4-diyl, (2,5-dipenthyl)phenyl-1,4-diyl, (2,5-dihexyl)phenyl-1,4-diyl, 2,5-bis(2-ethylhexyl) phenyl-1,4-diyl, (2,5-dimethoxy)phenyl-1,4-diyl, (2,5-diethoxy)phenyl-1,4-diyl, (2,5-dipropoxy)phenyl-1,4-diyl, (2,5-diisoprooxy)phenyl-1,4-diyl, (2,5-dibutoxy)phenyl-1,4-diyl, (2,5-dipenthyloxy)phenyl-1,4-diyl, (2,5-dihexyloxy)phenyl-1,4-diyl, 2,5-bis(2-ethylhexyloxy)phenyl-1,4-diyl. The preferred examples of Ar: thienyl-2,5-diyl, phenyl-1,4-diyl and (2,5-dimethyl)phenyl-1,4-diyl.

In the context of the present invention $Ar_n$ refers to any combination of n fragments of identical or different Ar, selected from the row described above. The preferred values of such combination are n identical unsubstituted thienyl-2,5-diyl fragment, linked to each other in the positions 2 and 5, for instance, 2,2'-bithienyl-2,5'-diyl (II-a-1), 2,2':5',2"-terthienyl-2,5"-diyl (II-a-2):

The other preferred value of such combination is a sequence of different unsubstituted or 2,5-substituted phenyl fragments, linked to each other in the positions 1 or 4, and different unsubstituted 1,3-oxazole-2,5-diyl fragments in such a way that their overall number is equal to n, for instance, when n=2 formula (II-1), when n=3 any of the formulas (II-2)-(II-4):

In the context of the present invention $Q_k$ refers to any combination of k fragments of identical or different Q, selected from the row described above. The preferred values of this combination are unsubstituted thienyl-2,5-diyl (II-a-3), unsubstituted phenyl-1,4-diyl (II-b-1), k identical unsubstituted thienyl-2,5-diyl fragments, linked to each other in the position 2 and 5, for instance, 2,2'-bithienyl-2,5'-diyl (II-b-1), 2,2':5',2''-terthienyl-2,5''-diyl (II-a-2):

In the context of the present invention $X_m$ refers to any combination of m fragments of identical or different X, selected from the row described above. The preferred values of such fragments are unsubstituted phenyl-1,4-diyl (II-b-1), unsubstituted 1,3-oxazole-2,5-diyl, unsubstituted thienyl-2,5-diyl (II-a-3), antracene-9,10-diyl (II-e), 1,3,4-oxadiazole-2,5-diyl (II-f), 2,1,3-benzothiadiazole-4,7-diyl.

In the context of the present invention $X_m(Q_k)_2$ refers to any combination of m fragments of identical or different X and k fragments of identical or different Q, selected from the rows described above. The preferred examples of the combinations of these fragments are: 2,1,3-benzothiodiazole-4,7-diylbis(thien-2,5-diyl) (II-5), 2,1,3-benzothiodiazole-4,7-diylbis(2,2'-bithien-5',5-diyl) (II-6), antracene-9,10-diylbis(phenylene-1,4-diyl) (II-7), antracene-9,10-diylbis(thien-2,5-diyl) (II-8), 2,2'-[1,4-phenylene]bis(1,3-oxazole-2,5-diyl-phenylene-4,1-diyl) (II-9), substituted fluorene-4,4'-diylbis(thien-2,5-diyl) (II-10):

-continued (II-10)

The positions, marked in the formulas (II-a-1)-(II-a-3) and (II-1)-(II-9) with a sign * (star) are the points in the molecules, in which the structural fragments (II-a)-(II-h) are linked to each other in the form of linear conjugated oligomer chains $Ar_n$, $X_m$, $Q_k$ or the ends of the chains $Ar_n$ or $X_m(Q_k)_2$, linked with silicon atoms in the points of branching or the terminal substituents R and $R_1$.

The described values for R, Ar, $Ar_n$, Q, $Q_k$, X, $X_m$ are particular cases and do not limit all possible combinations of n, m, k for the values of Ar, Q, X between them.

In particular, in the formula (I) Ar may stand for thienyl-2,5-diyl, selected from a number of the compounds of the formula (II-a), then the general formula has a following structure:

(I-a)

where X, Q, R, $R_1$, $R_2$, n, m, k have the values described above.

In particular, in the formula (I) Ar may stand for phenyl-1,4-diyl, selected from a number of compounds with the formula (II-b), then the general formula has the following structure:

(I-b)

where X, Q, R, $R_3$, $R_4$, n, m, k have the values described above.

In particular, in the formula (I) X may stand for substituted fluorene-4,4'-diyl (II-d), when Q stands for thienyl-2,5-diyl, selected from a number of compounds with the formula (II-a), m is equal to 1, k is equal to 1, then the general formula has the following structure:

(I-c)

where Ar, R, $R_6$, $R_7$ and n have the values described above.

Figure 3:
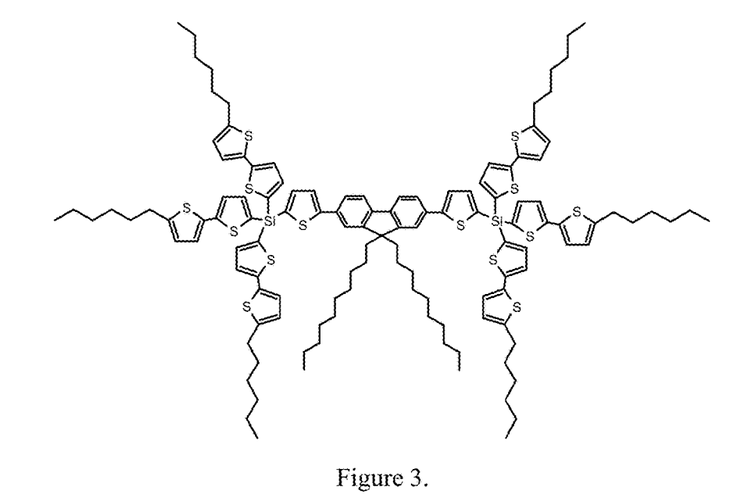
In FIG. 3 a schematic representation of the structural formulae of the novel branched oligoarylsilane I-1 (according to example 4) is shown.

In this case, for instance, when Ar=unsubstituted thienyl-2,5-diyl, $R=C_6H_{13}$, $R_6=R_7=C_{10}H_{21}$, n=2, the novel branched oligoarylsilane (FIG. 3) may be described by the formula (I-1):

(I-1)

In particular, in the formula (I) X may stand for phenyl-1,4-diyl (II-b) and 1,3-oxazole-2,5-diyl (II-c), when Q stands for phenyl-1,4-diyl, selected from a number of compounds with the formula (II-b), m is equal to 3, k is equal to 1, then the general formula has the following structure:

(I-d)

where Ar, R, $R_3$, $R_4$, $R_5$ and n have the values described above.

In particular, in the formula (I) n may be is equal to 2, then the general formula has the following structure:

$X_m$—[$Q_k$-Si-(-$Ar_2$—R)$_3$]$_2$ (I-e)

where R, Ar, X, Q, k and m have the values described above.

In particular, in the formula (I) n may be is equal to 3, then the general formula has the following structure:

$X_m$—[$Q_k$-Si-(-$Ar_3$—R)$_3$]$_2$ (I-f)

where R, Ar, X, Q, k and m have the values described above.

Figure 4:
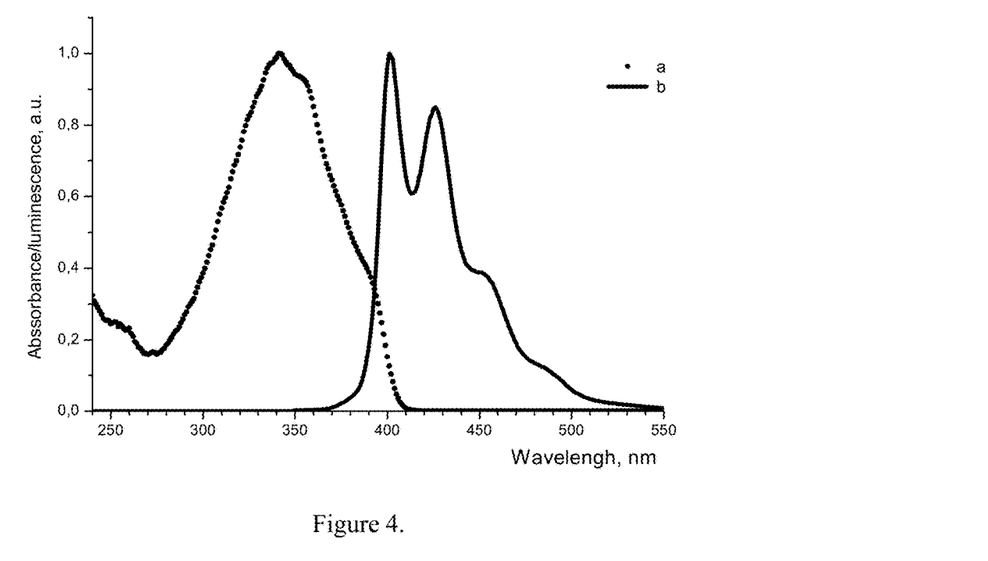
In FIG. 4 absorption (a) and luminescence (b) spectra of the novel branched oligoarylsilane I-1 in diluted THF (tetrahydrofurane) solution are shown.

The novel branched oligoarylsilanes claimed contain identical or different aryl- or heteroarylsilane groups, which exhibit efficient luminescence. This may be illustrated by the absorption and luminescence spectra of their dilute solutions (see, for instance, FIG. 4). As can be seen from the spectral data, the novel branched oligoarylsilanes claimed possess a wide absorption spectrum with two characteristic maxima, a high luminescence quantum yield and efficient intramolecular energy transfer. A high quantum yield in the present invention refers to a luminescence quantum yield in dilute solution equal to or above 50%, preferably exceeding 70%. An efficient intramolecular energy transfer refers to an efficiency of no less than 70%, preferably no less than 90%. The data described gives only some examples of the claimed branched oligoarylsilanes, and does not limit their potential properties at all.

A characteristic feature of the oligoarylsilanes claimed is their high thermal stability, defined within the present invention as the temperature of 1% weight loss during the compound heating under argon atmosphere. This temperature for different particular cases is no less than 200° C., preferably no less than 400° C.

A solution is also provided by elaborated method of synthesis of novel branched oligoarylsilanes of general formula (I). This method can be briefly described as follows. A compound of general formula (III)

(III)

where Y stands for the residue of boric acid or its ester, or Br, or I,

R, Ar, Q, n, k have the values pointed above, react under Suzuki conditions with a reagent of general formula (IV)

(IV), where A stands for Br or I, provided that Y stands for the residue of boric acid or its ester, or for the residue of boric acid or its ester, provided that Y stands for Br or I.

X, m have the values pointed above.

Under Suzuki reaction we understand a reaction of aryl- or heteroaryl-halogenide with aryl- or heteroaryl-organoboronic compound (Suzuki, Chem. Rev. 1995. V.95. P. 2457-2483) in the presence of a base and a catalyst, containing metal of the VIII subgroup of periodic table. It's well known that for this reaction any available base can be used, such as hydroxides, for instance, NaOH, KOH, LiOH, $Ba(OH)_2$, $Ca(OH)_2$; alkoxides, for instance, NaOEt, KOEt, LiOEt, NaOMe, KOMe, LiOMe; alkali metal salts of carbonic acids, for instance, carbonates, hydrocarbonates, acetates, cytrates, acetylacetonates, sodium, potassium or lithium glicinates, for instance, $Cs_2CO_3$, $Tl_2CO_3$; phosphates, for instance, sodium, potassium or lithium phosphates. The preferred base is sodium carbonate. Bases are used in the form of water solutions or suspensions in organic solvents, such as toluene, dioxane, ethanole, dimethylformamide or their mixtures. Water-based solutions are preferred. Also any compounds, containing metals of VIII subgroup of Periodic table may be used as the catalysts in Suzuki reaction. The preferred metals are Pd, Ni, Pt. The most preferred metal is Pd. Catalyst or catalysts preferably are used in the amounts ranging from 0.01 mol % to 10 mol %. The most preferable amount of the catalyst is between 0.5 mol % and 5 mol % in respect to the molar amount of the reagent with the lower molar mass. The most available catalysts are complexes of VIII subgroup metals. In particular, stable in air conditions palladium (0) complexes, palladium complexes, which are reduces directly in the reaction vessel by organometallic compounds (alkyllithium or organomagnesium compounds) or phosphines to palladium (0), such as palladium(II) complexes with triphenylphosphine or other phosphines. For instance, $PdCl_2(PPh_3)_2$, $PdBr_2(PPh_3)_2$, $Pd(OAc)_2$ or their mixtures with triphenylphosphine. It is preferable to use commercially available $Pd(PPh_3)_4$ with or without additionally added phosphines. As phosphines it is preferable to use $PPh_3$, $PEtPh_2$, $PMePh_2$, $PEt_2Ph$, $PEt_3$. The most preferable is triphenylphosphine.

A general scheme of the process may be depicted as following:

where A, X, Y, Q, Ar, R, n, m and k have the values pointed above.

In particular, Y for a compound of formula (III) may stand for the residue of the cyclic ester of boronic acid—4,4,5,5-tetramethyl-1,3,2-dioxaborolane of general formula (V)

(V)

in this case a branched oligoarylsilane is obtained according to the following general scheme:

where A, X, Q, Ar, R, n, m, and k have the values pointed above.

In particular, for a compound of formula (IV) A may stand for Br, then a branched oligoarylsilane is obtained according to the following general scheme:

where X, Y, Q, Ar, R, $R_1$, n, m and k have the values pointed above.

In particular, for a compound of formula (IV) X may stand for substituted fluorene-4,4'-diyl (II-d), under condition that Q stands for thienyl-2,5-diyl, selected from a number of compounds of formula (II-a), m is equal to 1, k is equal to 1, then the branched oligoarylsilane is obtained according to the following general scheme:

where A, Y, Ar, R, $R_6$, $R_7$, n have the values pointed above.

In particular, for a compound of formula (IV) X may stand for phenyl-1,4-diyl (II-b) and 1,3-oxazole-2,5-diyl(II-c), under condition that Q stands for phenyl-1,4-diyl, selected from a number of compounds of formula (II-b), m is equal to 3, k is equal to 1, then the branched oligoarylsilane is obtained according to the following general scheme:

where A, Y, Ar, R, $R_3$, $R_4$, $R_5$, n have the values pointed above.

The reactions described above may be carried out in organic solvents or mixtures of solvent which do not interact with the reacting species. For instance, a reaction can be carried out in a medium of an organic solvent, selected from a number of ethers: tetrahydrofurane, dioxane, dimethyl ether of ethylene glycol, diethyl ether of ethylene glycol, dimethyl ether of ethylene glycol; otherwise, from a number of aromatic compounds: benzene, toluene, xylene, or from a number of alkanes: pentane, hexane, heptane, or from a number of alcohols: methanol, ethanol, isopropanol, butanol, or from the row aprotic polar solvents: dimethyl formamide, dimethyl sulfoxide. A mixture of two or more solvents may be used as well. The most preferred solvents are toluene, tetrahydrofurane, ethanol, dimethyl formamide or their mixtures. In these cases the initial components may react at temperatures ranging from +20° C. to +200° C. under a stoichiometric molar ratio between functional groups of the initial components or an excess of one of them. The reaction is preferably conducted at temperatures ranging from +40° C. to +150° C. The most preferred temperature region for the reaction is between +60° C. and +120° C.

After completion of the reaction, the product is isolated according to the known methods. For instance, water and an organic solvent are added. The organic phase is separated, washed with water until the pH is neutral and dried, after that the solvent is evaporated. As an organic solvent any immiscible or limitedly miscible with water solvent may be used, for instance, selected from a number of ethers: diethyl ether, methyltertbutyl ether, or selected from a number of aromatic compounds: benzene, toluene, xylene, or selected from a number of organochlorine compounds: dichloromethane, chloroform, carbon tetrachloride, chlorobenzene. Moreover, organic solvent mixtures may be used for the isolation. Isolation of the product may be performed also without organic solvents, for instance, via solvents evaporation from the reaction mixture, separation of the product from the water-based layer via filtration, centrifugation, or any other known method.

Purification of the raw product is performed by any known method, for instance, preparative chromatography in adsorption or exclusion regime, recrystallization, fractional precipitation or fractional dissolution, or any their combination.

Figure 5:
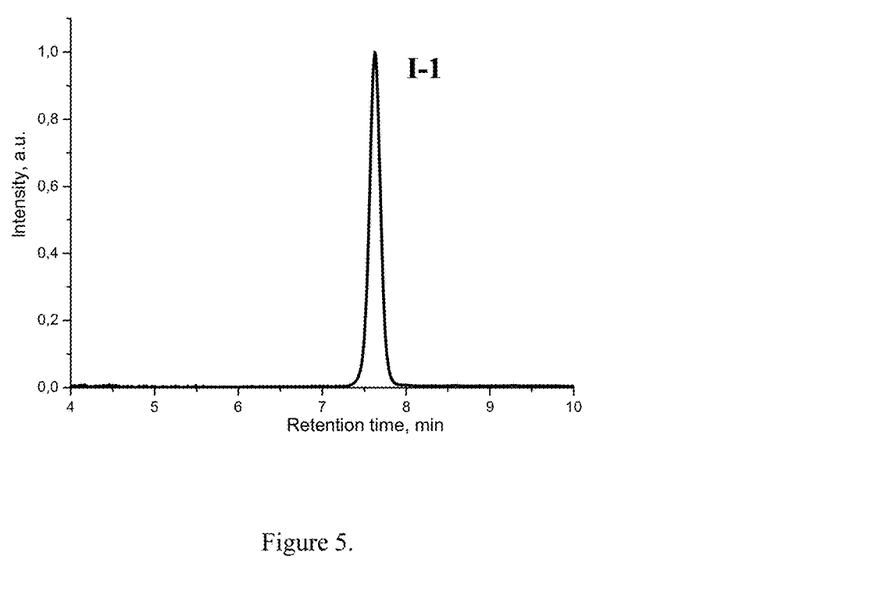
In FIG. 5 a GPC curve of pure compound I-1 is shown.

Purity and molecular structure of the compounds synthesized is confirmed by a combination of physical and chemical analyses data well known for the skilled persons, such as chromatographic, spectroscopic, mass-spectroscopic, elemental analysis. The most preferred purity and molecular structure confirmation of novel branched oligoarylsilanes are $^1$H, $^{13}$C and $^{29}$Si NMR-spectra, as well as GPC (gel permeation chromatography). GPC curves of a novel branched oligoarylsilane correspond to a narrow monodisperse molecular weight distribution (see, for instance, FIG. 5).

The invention may be illustrated by the following examples. Commercially available reagents and solvents were used. The initial reagent 5-hexyl-2,2'-bithiophene was prepared according to the known methods (S. Gronowitz, A.-B.-Hornfeldt, Thiophenes, Elsevier Academic press, 2004, pp. 755). Other initial compounds were prepared according to the following examples. All the reactions were carried out in anhydrous solvents under argon atmosphere.

Synthesis of the Starting Reagents

Example 1. Synthesis of 2-thienyltrimethoxysilane (VI)

To 27.73 ml (0.069 mol) of 2.5M solution of n-butyllithium in hexane at 0° C. 7.00 g (0.083 mol) of thiophene were added dropwise. The resulting lithium derivative of thiophene was added to 40 ml (0.166 mmol) tetraethoxysilane solution in 40 ml THF at 0° C. After vacuum distillation ($T_b$=120° C./10 mbar) 7.07 g (34% from the theory) of compound VI were obtained. $^1$H NMR (CDCl$_3$): 1.27 (t, 9H, J=6.7 Hz), 3.90 (q, 6H, J$_1$=6.7 Hz), 7.23 (dd, 1H, J$_1$=3.7 Hz, J$_2$=4.9 Hz), 7.50 (d, 1H, J=3.7 Hz), 7.67 (d, 1H, J=4.9 Hz).

Example 2. Synthesis of (2-thienyl)[tris(5'-hexyl-2, 2'-bithienyl-5-yl)]silane (VII)

5.28 ml (13 mmol) of 2.5M n-butyllithium solution in hexane were added to a solution of 3.3 g (13.2 mmol) of 5-hexyl-2,2'-bithiophene in 60 ml THF at −78° C. After that 1.03 g (0.42 mmol) of compound VI were added. In 30 minutes of stirring of the reaction mixture under cooling the reaction yield was 55% (according to GPC). After a standard isolation procedure and purification by means of column chromatography the chromatographically pure product yield was 1.59 g (44% from the theory). $^1$H NMR (250 MHz, δ in DMSO, TMS/ppm.): 0.89 (t, 9H, J=6.7 Hz), 1.25-1.45 (overlapping signals, 18H), 1.66 (m, 6H, M=5, J=6.7 Hz), 2.77 (t, 6H, J=7.3 Hz), 6.69 (dd, 3H, J$_1$=3.7 Hz, J$_2$=1.2 Hz), 7.03 (d, 3H, J=3.7 Hz), 7.23 (d, 3H, J=3.7 Hz), 7.29 (dd, 1H, J$_1$=3.7 Hz, J$_2$=4.3 Hz), 7.33 (d, 3H, J=3.7 Hz), 7.51 (d, 1H, J=3.7 Hz), 7.90 (d, 1H, J=4.3 Hz).

Example 3. Synthesis of tris(5'-hexyl-2,2'-bithien-5-yl)[5'-(4,4,5,5-tetramethyl-1,3,2-dioxyborolane-2-yl)-2,2'-bithien-5-yl]silane (III-1)

1.1 ml (1.7 mmol) of 1.6M BuLi solution in hexane were added dropwise to a solution of 1.5 g (1.7 mmol) of compound VII in 40 ml THF, maintaining the temperature below −80° C. After that 0.36 ml (1.7 mmol) of 2-isopropoxy-4,4,5,5-tetramethyl-1,3,2-dioxyborolane were added. The temperature was risen up to the room temperature, and 200 ml of distilled water, 300 ml of diethyl ether and 2 ml of 1N HCl water solution were added. After a standard isolation of the product, the yield of chromatographically pure product was 1.70 g (97% from the theory). $^1$H NMR (δ in DMSO-CCl$_4$, TMS/ppm.): 0.89 (9H, t, J=6.7 Hz), 1.23-1.41 (30H, overlapping peaks), 1.65 (6H, m, M=5, J=7.3), 2.77 (6H, t, J=7.3 Hz), 6.69 (3H, d, J=3.7 Hz), 7.05 (3H, d, J=3.7 Hz), 7.22 (3H, d, J=3.7 Hz), 7.33 (3H, d, J=3.7 Hz), 7.56 (1H, d, J=3.7 Hz), 7.67 (1H, t, J=3.7 Hz).

Synthesis of Novel Branched Oligoarylsilanes

A General Method of the Synthesis of Branched Oligoarylsilanes:

0.45 mmol of compound IV, 0.05 mmol catalyst, containing VIII subgroup of Periodic table metals, and 3.0 mmol base are added to a solution of 1.0 mmol of compound III in toluene. The mixture is stirred during several hours at 80° C.-120° C. After the reaction completion the product is isolated according to the known methods. The product is purified by means of column chromatography on silica gel.

Example 4. Synthesis of the Novel Branched Oligoarylsilane (I-1)

Branched oligoarylsilane I-1 was prepared according to the general synthetic method from 1.62 g of compound III-1, 0.45 g of 4,4'-dibromo-9,9-didecylfluorene, 0.095 g of the catalyst Pd(PPh$_3$)$_4$, 3 ml of 2M Na$_2$CO$_3$ aqueous solution and 40 ml of toluene. After isolation and purification 0.549 g (35% from the theory) of pure branched oligoarylsilane (I-1) were obtained. $^1$H NMR (δ in DMSO-CCl$_4$, TMS/ppm.): 0.51-0.61 (overlapping signals, 4H), 0.78 (t, 6H, J=6.7 Hz), 0.89 (18H, t, J=6.7 Hz), 0.96-1.15 (overlapping signals, 28H), 1.23-1.41 (36H, overlapping peaks), 1.65 (12H, m, M=5, J=7.3), 1.96-2.03 (overlapping signals, 4H), 2.77 (12H, t, J=7.3 Hz), 6.69 (6H, d, J=3.7 Hz), 7.05 (6H, d, J=3.7 Hz), 7.25 (6H, d, J=3.7 Hz), 7.39 (6H, d, J=3.7 Hz), 7.47 (d, 2H, J=3.7 Hz), 7.58 (4H, s), 7.64 (2H, d, J=7.9 Hz), 7.73 (2H, d, J=7.9 Hz).

Examples 5-15. Synthesis of Novel Branched Oligoarylsilanes (I-2-I-12)

Synthesis of novel branched oligoarylsilanes I-2-I-12 was performed according to the general method from initial reagents under conditions described in Table 1. As a catalyst Pd(PPh$_3$)$_4$ was used, while as a base—2M Na$_2$CO$_3$ aqueous solution similarly to example 4.

Although the best mode contemplated by the inventors of carrying out the present invention is disclosed above, practice of the above invention is not limited thereto. It will be manifest that various additions, modifications and rearrangements of the features of the present invention may be made without deviating from the spirit and the scope of the underlying inventive concept.

What is claimed is:

1. A method of preparation of branched oligoarylsilanes of formula (I), where R stands for a substituent from a group including: linear or branched $C_1$-$C_{20}$ alkyl groups; linear or branched $C_1$-$C_{20}$ alkyl groups, separated by at least one oxygen atom; linear or branched $C_1$-$C_{20}$ alkyl groups, separated by at least one sulfur atom; branched $C_3$-$C_{20}$ alkyl groups, separated by at least one silicon atom; $C_2$-$C_{20}$ alkenyl groups,

Ar stands for identical or different arylene or hetetoarylene radicals, selected from a group including: substituted or unsubstituted thienyl-2,5-diyl of formula (II-a)

(II-a)

substituted or unsubstituted phenyl-1,4-diyl of formula (II-b)

(II-b)

substituted or unsubstituted 1,3-oxazole-2,5-diyl of formula (II-c)

(II-c)

substituted fluorene-4,4'-diyl of formula (II-d)

(II-d)

substituted cyclopentathiophene-2,7-diyl of formula (II-e)

where $R_1$, $R_2$, $R_3$, $R_4$, $R_5$, independently on each other stand for H or a substituent from the aforementioned group for R; $R_6$, $R_7$, $R_8$, $R_9$ stands for a substituent from the aforementioned group for R, Q stands for a radical from the aforementioned group for Ar,

X stands for at least one radical, selected from the aforementioned group for Ar and/or a radical from the group: 2,1,3-benzothiodiazole-4,7-diyl (II-f)

of formula (II-f), antracene-9,10-diyl of formula (II-g)

(II-g)

1,3,4-oxadiazole-2,5-diyl of formula (II-h)

(II-h)

1-phenyl-2-pyrazoline-3,5-diyl of formula (II-i)

(II-i)

perylene-3,10-diyl of formula (II-j)

(II-j)

n stands for an integer from the group from 2 to 4, m stands for an integer from the group from 1 to 3, k stands for an integer from the group from 1 to 3, the method comprising:

a compound of general formula (III)

$$Y-Q_k-Si(-Ar_n-R)_3$$ (III)

reacting under Suzuki conditions, where Y stands for a residue of boronic acid or its ester, or Br, or I,
R, Ar, Q, n, k have the aforementioned values,
with a reagent of general formula (IV)

$$A\text{-}X_m\text{-}A \qquad (IV),$$

where A stands for:
Br or I, if Y stands for a residue of boronic acid or its ester, or
a residue of boronic acid or its ester, if Y stands for Br or I; and
X and m have the aforementioned values.

2. The method according to claim 1, wherein a boronic ester is an ester, selected from a group including: 4,4,5,5-tetramethyl-1,3,2-dioxaborolane of formula (V-a)

(V-a)

1,3,2-dioxaborolane of formula (V-b)

(V-b)

b) 1,2,3-dioxaborinane of formula (V-c)

(V-c)

5,5-dimethyl-1,2,3-dioxaborinane of formula (V-d)

(V-d)

3. The method according to claim 1, wherein A in the compound of formula (IV) stands for Br.

4. The method according to claim 1, wherein X stands for substituted fluorene-4,4'-diyl (II-d), under condition that Q stands for thienyl-2,5-diyl, selected from a number of compounds corresponding to the formulae (II-a), m is equal to 1, k is equal to 1.

5. The method according to claim 1, wherein X stands for phenyl-1,4-diyl (II-b) and 1,3-oxazole-2,5-diyl (II-c), under condition that Q stands for phenyl-1,4-diyl, selected from a number of compounds corresponding to the formulae (II-c), m is equal to 3, k is equal to 1.

6. The method according to claim 1, wherein the reaction of components is carried out at temperatures ranging from 20 to 200° C.

7. The method according to claim 1, wherein the reaction of components is carried out in a medium of an organic solvent, selected from a group including toluene, tetrahydrofuran, ethanol, dioxane, dimethylformamide or their mixtures.

8. The method according to claim 1, wherein the branched oligoarylsilanes obtained possess a luminescence quantum yield of no less than 50%.

9. The method according to claim 1, wherein the branched oligoarylsilanes obtained possess an intramolecular energy transfer efficiency of no less than 70%.

10. The method according to claim 1, wherein the branched oligoarylsilanes obtained are thermally stable up to temperatures of no less than 200° C.

* * * * *